United States Patent
Dyhrfjeld-Johnsen (10) Patent No.: US 10,188,695 B2
(45) Date of Patent: Jan. 29, 2019

(54) CALCINEURIN INHIBITORS FOR USE IN THE TREATMENT OF LESIONAL VESTIBULAR DISORDERS

(71) Applicants: Institut National De La Santé Et De La Recherche Médicale, Paris (FR); Sensorion, Montpellier (FR)

(72) Inventor: Jonas Dyhrfjeld-Johnsen, Montpellier (FR)

(73) Assignees: Sensorion, Montpellier (FR); INSERM, Paris (FR)

( * ) Notice: Subject to any disclaimer, the term of this patent is extended or adjusted under 35 U.S.C. 154(b) by 0 days.

(21) Appl. No.: 14/380,652

(22) PCT Filed: Feb. 22, 2013

(86) PCT No.: PCT/EP2013/053557
§ 371 (c)(1),
(2) Date: Aug. 22, 2014

(87) PCT Pub. No.: WO2013/124416
PCT Pub. Date: Aug. 29, 2013

(65) Prior Publication Data
US 2015/0057233 A1    Feb. 26, 2015

Related U.S. Application Data

(60) Provisional application No. 61/602,357, filed on Feb. 23, 2012.

(30) Foreign Application Priority Data

Feb. 23, 2012  (EP) ..................................... 12156647

(51) Int. Cl.
| A61K 31/436 | (2006.01) |
| A61K 38/13 | (2006.01) |
| A61K 31/505 | (2006.01) |
| A61K 31/439 | (2006.01) |
| A61K 31/50 | (2006.01) |

(52) U.S. Cl.
CPC ............ *A61K 38/13* (2013.01); *A61K 31/436* (2013.01); *A61K 31/439* (2013.01); *A61K 31/50* (2013.01); *A61K 31/505* (2013.01)

(58) Field of Classification Search
CPC .... A61K 38/13; A61K 31/436; A61K 31/439; A61K 31/50; A61K 31/505
See application file for complete search history.

(56) References Cited

U.S. PATENT DOCUMENTS

2003/0229333 A1* 12/2003 Ashton ................. G06Q 50/22
                                                      604/514
2004/0077676 A1*  4/2004 Matsuoka .......... A61K 31/4745
                                                      514/291
2009/0186422 A1   7/2009 Hogan et al.
2009/0306225 A1  12/2009 Lichter et al.
2010/0203120 A1*  8/2010 Coulter ................ A61K 9/5015
                                                      424/452
2010/0215737 A1*  8/2010 Coulter ................ A61K 9/5015
                                                      424/456

FOREIGN PATENT DOCUMENTS

| CA | 2709132 | 1/2012 |
| EP | 1975174 | 10/2008 |
| WO | 2009048929 | 4/2009 |
| WO | WO 2009/105755 | 8/2009 |
| WO | WO 2012/026665 A1 | 3/2012 |

OTHER PUBLICATIONS

Erdmann et al., The Novel Calcineurin Inhibitor CN585 Has Potent Immunosuppressive Properties in Stimulated Human T Cells, Jl. Biol. Chem. vol. 285, No. 3 pp. 1888-1898, Jan. 15, 2010.*
PDF of web page from http://medical-dictionary.thefreedictionary.com/Vestibular+organ, date 2016.*
Erdmann et al., The Novel Calcineurin Inhibitor CN585 Has Potent Immunosuppressive Properties in Stimulated Human T Cells, The Journal of Biological Chemistry vol. 285, No. 3, pp. 1888-1898, Jan. 15, 2010.*
Elidan et al., Effect of Cyclosporine A on the Hearing Loss in Behcet's Disease, Ann Otol Rhinol Laryngol 100:1991, 464-468.*
Naesens et al., Clin J Am Soc Nephrol 4: 481-508, 2009.*
Dixon et al., Journal of Neurotrauma 33:553-566 (Mar. 15, 2016).*
Horii et al., Microarray analysis of gene expression in the rat vestibular nucleus complex following unilateral vestibular deafferentation, Journal of Neurochemistry, 2004, 91, 975-982.*
Fetoni et al, "Protective effects of alpha-tocopherol against gentamicin-induced Oto-vestibulo toxicity: an experimental study Acta Otolaryngol", Jan. 2003;123(2):192-7.
Figge et al. "Neurite outgrowth triggered by the cell adhesion molecule L1 requires activation and inactivation of the cytoskeletal protein cofilin", 2012, Mol cell Neurosci, 49(2):196.
Sieber et al. "Novel inhibitors of the calcineurin/NFATc hub—alternatives to CsA and FK506?" Cell Commun Signal. Oct. 27, 2009;7:25.
Strupp and Brandt, "Vestibular neuritis", Semin Neurol. Nov. 2009;29(5):509-19.
ISR of the International patent application WO2013/124416.
Birsan et al., "The novel calcineurin inhibitor ISA247: a more potent immunosuppressant than cyclosporine in vitro". Transpl Int. May 2005;17(12):767-71.
Kumagami et al., "Expression pattern of adenylyl cyclase isoforms in the inner ear of the rat by RT-PCR and immunochemical localization of calcineurin in the organ of Corti". Hear Res. Jun. 1999;132(1-2):69-75.
Almawi et al., "Clinical and mechanistic differences between FK506 (tacrolimus) and cyclosporin A". Nephrol Dial Transplant. Dec. 2000;15(12):1916-8.

(Continued)

*Primary Examiner* — Sudhakar Katakam
(74) *Attorney, Agent, or Firm* — Entralta P.C.; James W. Collett; Peter D. Weinstein (57) ABSTRACT

The present invention relates to a calcineurin inhibitor for use in the treatment of a lesional vestibular disorder.

9 Claims, 3 Drawing Sheets
Specification includes a Sequence Listing.

(56) References Cited

OTHER PUBLICATIONS

Farrell, Perhiperal versus central cestibular disorders, Fact sheet american physical therapy association, available online, 2018, http://www.neuropt.org/docs/vsig-physician-fact-sheets/peripheral-vs-central-vestibular-disorders.pdf.

FDA Guidance for industry, Estimating the maximum safe starting dose in initial clinical trials for therapeutics in adult healthy volunteers, U.S. department of health and human services food and drug administration center for drug evaluation and research (C.D.E.R.), 2005, 1-17.

Furst, Efficacy of tacrolimus in rhematoid arthritis patients who have been treated unsuccessfully with methotrexate, Arthritis and rheumatism, vol. 46, 8, 2002, 2020-2028.

Netter, Vestibulocochlear Nerve (VIII): Schema, Atlas of human anatomy, plate 125, Elsevier, 6th Edition, 2014.

Yocum, Safety of tacrolimus in patients with rhumatoid arthritis: long term experience, Rheumatology, vol. 43, 2004, 992-999.

\* cited by examiner

SEQUENCE LISTING

```
<160> NUMBER OF SEQ ID NOS: 12

<210> SEQ ID NO 1
<211> LENGTH: 15
<212> TYPE: PRT
<213> ORGANISM: Artificial Sequence
<220> FEATURE:
<223> OTHER INFORMATION: LxVPc1 peptide

<400> SEQUENCE: 1

Asp Gln Tyr Leu Ala Val Pro Gln His Pro Tyr Gln Trp Ala Lys
1               5                   10                  15
```

```
<210> SEQ ID NO 2
<211> LENGTH: 15
<212> TYPE: PRT
<213> ORGANISM: Artificial Sequence
<220> FEATURE:
<223> OTHER INFORMATION: LxVPc3 peptide

<400> SEQUENCE: 2

Asp Gln Phe Leu Ser Val Pro Ser Pro Phe Thr Trp Ser Lys Pro
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: LxVPc4 peptide

<400> SEQUENCE: 3

Met Asp Tyr Leu Ala Val Pro Ser Pro Leu Ala Trp Ser Lys Ala
1               5                   10                  15

<210> SEQ ID NO 4
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD shRNA"
      /organism="Artificial Sequence"

<400> SEQUENCE: 4
cucacuacca aauguuaau                                                    19

<210> SEQ ID NO 5
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD shRNA"
      /organism="Artificial Sequence"

<400> SEQUENCE: 5
gagugaccuu cgcuccaca                                                    19

<210> SEQ ID NO 6
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD shRNA"
      /organism="Artificial Sequence"

<400> SEQUENCE: 6
gaguuugugg acuccuuua                                                    19

<210> SEQ ID NO 7
<211> LENGTH: 19
<212> TYPE: RNA
<213> ORGANISM: Artificial Sequence
```

```
<220> FEATURE:
<221> NAME/KEY: source
<222> LOCATION: 1..19
<223> OTHER INFORMATION: /mol_type="unassigned RNA"
      /note="BAD shRNA"
      /organism="Artificial Sequence"

<400> SEQUENCE: 7
gugcucacua ccaaauguu                                              19

<210> SEQ ID NO 8
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD shRNA"
      /organism="Artificial Sequence"

<400> SEQUENCE: 8
gacuuggacu uggauguaa                                              19

<210> SEQ ID NO 9
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD siRNA"
      /organism="Artificial Sequence"

<400> SEQUENCE: 9
gaucggaacu ugggcaggg                                              19

<210> SEQ ID NO 10
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD siRNA"
      /organism="Artificial Sequence"

<400> SEQUENCE: 10
cagaguuuga gccgaguga                                              19

<210> SEQ ID NO 11
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD siRNA"
      /organism="Artificial Sequence"

<400> SEQUENCE: 11
gagcuccgga ggaugagug                                              19
```

```
<210> SEQ ID NO 12
<211> LENGTH: 19
<212> TYPE: RNA
<213> ORGANISM: Artificial Sequence
<220> FEATURE:
<221> NAME/KEY: source
<222> LOCATION: 1..19
<223> OTHER INFORMATION: /mol_type="unassigned RNA"
      /note="BAD siRNA"
      /organism="Artificial Sequence"

<400> SEQUENCE: 12
uuguggacuc cuuuaagaa                                                19
```

CALCINEURIN INHIBITORS FOR USE IN THE TREATMENT OF LESIONAL VESTIBULAR DISORDERS

CROSS-REFERENCE TO RELATED APPLICATIONS

This application is a U.S. National Phase of PCT Patent Application No. PCT/EP2013/053557 filed Feb. 22, 2013 and claims priority to European Patent Application No. EP 12156647.5 filed Feb. 23, 2012 and U.S. Provisional Patent Application No. 61/602,357 filed Feb. 23, 2012, the disclosures of which are incorporated herein by reference in their entirety for all purposes.

FIELD OF INVENTION

The present invention relates to calcineurin inhibitors for use in the treatment of lesional vestibular disorders.

BACKGROUND OF INVENTION

Introduction on Vestibular Disorders

Vestibular (inner ear) disorders can cause dizziness, vertigo, imbalance, hearing changes, nausea, fatigue, anxiety, difficulty concentrating, and other symptoms, with potentially devastating effects on a person's day-to-day functioning, ability to work, relationships with family and friends, and quality of life.

For example, vestibular neuritis is the primary cause of hospitalisation for non neurological vertigos. Because its aetiology is largely unknown, epidemiological studies are variable depending on the source (the incidence is believed to be between 3.5 and 50 new cases for 100000 persons/per year). In the past, either an inflammation of the vestibular nerve, a reactivation of herpes simplex virus type 1 or labyrinthine ischemia was proposed as a cause of vestibular neuritis. Currently, a viral cause is favoured. A reactivation of herpes simplex virus type 1 would explain the repetition of the vertigo crisis under such circumstances. However, only the involvement of inflammatory pathophysiological mechanisms has been established.

Vestibular disorders may be also involved in the majority of the falls in the elderly population and their prevention has become a priority. The falls in the elderly population indeed represents more than 1% of the total budget of the health insurance in France (INSEE 1990), affecting 30% of people above 65 and 50% above 80. Falls in the elderly population are involved in ⅔ of deaths caused by accident above 65, increasing the risk of death by a factor of 4 in a given year.

Aetiology of Vestibular Disorders

Although the aetiology of vestibular disorders is mostly unknown, it is widely accepted that vestibular disorders constitute a vast family of conditions wherein the vestibular organ is associated. These disorders may be distinguished by their putative origins, one can thus identify (1) lesional vestibular disorders and (2) non lesional vestibular disorders.

1) Lesional vestibular disorders refer to vestibular disorders wherein lesions of inner ear cells and/or vestibular nerve are present or will appear during the disorder time course. In this case, the functionality of the vestibule is impaired as it can be observed using clinical functional tests (VOR, VNG). Lesional vestibular disorders include:

vestibular disorders wherein an inflammation of the inner ear and/or the vestibular nerve induces reversible and/or irreversible damages. One example of conditions from this group is vestibular neuritis;

vestibular disorders wherein inner ear fluids are affected (abnormalities in the quantity, composition, and/or pressure of the endolymph), these disorders usually develop lesions during the disease time course. Examples of conditions from this group are Menière's disease and secondary endolymphatic hydrops. They are currently associated with tinnitus and hearing loss;

vestibular disorders induced by insults or lesions of the vestibular endorgans. Examples of said conditions are vertigo caused by local ischemia, excitotoxicity, trauma that affect temporal bones or ototoxic insult to vestibular hair cells by drugs such as gentamicin and cisplatin.

2) Non-lesional vestibular disorders refer to vestibular disorders supported by transient and often iterative vertigo crisis wherein no lesion on inner ear cells and/or vestibular nerve can be observed. In this case, the functionality of the vestibule evaluated between the vertigo crisis using functional tests (VOR, VNG) does not differ from healthy vestibule. Non-lesional vestibular disorders include:

vestibular disorders wherein debris had been collected within a part of the inner ear. This debris, called otoconia, is made up of small crystals of calcium carbonate and when they shift, they send false signals to the brain. Examples of said conditions are positional vertigos;

iterative vestibular disorders of unknown origin without tinnitus or hearing loss.

Evaluation of the Vestibule Functional Loss

In patients, morphofunctional alterations of the vestibular endorgans cannot be evaluated directly (except for large lesions that can be detected by MRI). Conversely, indirect assessment methods are currently used to evaluate the loss of functionality of the vestibule. These testing methods are generally conducted at ENT clinic/hospitals. Among them we can cite the vestibulonystagmography (VNG) and assessment of the vestibuloocculomotor reflex (VOR) using caloric or rotational tests, head impulse testing (HIT) and vestibular evoked myogenic potentials (VEMP).

Treatments of Vestibular Disorders

Current treatment of vestibular disorders mainly focus on reducing the vertigo crisis using vestibuloplegic drugs, while limiting neurovegetative reactions by using anti emetic drugs. Corticosteroids and antiviral drugs are the only medication used indirectly in an attempt to limit the spread of vestibular damages in the case of vestibular neuritis (if assumed to be due to bacterial or virus infections), by treating the putative cause of the vestibular dysfunction. Their effect remains under debate due to the lack of established aetiology in most vestibular deficits and have been suggested to only improve resolution of the initial peak crisis without improving long term patient outcome. For example, recovery after vestibular neuritis is usually incomplete. In a study of 60 patients, horizontal semicircular canal paresis was found in about 90% one month after the onset of symptoms, and in 80% after six months; the caloric responses eventually normalized in only 42%. On the basis of the incidence of this condition, a substantial and permanent unilateral dynamic deficit of the vestibulo ocular reflex, which cannot be completely compensated for by other mechanisms, develops in approximately 4000 person per year in the United States. This deficit leads to impaired vision and postural imbalance during walking and especially during head movement toward the affected ear.

Accordingly, there is a need for a protective or reparative therapy that prevents, reduces or treats the incidence and/or severity of lesional vestibular disorders, said functional alteration of the inner ear cells and/or vestibular nerve being due to inflammations, lesions or insults of diverse origins.

The inventors surprisingly found that calcineurin inhibitors were able to prevent or treat vestibular lesions by protecting inner ear cells and vestibular nerve from damage or degeneration.

SUMMARY

The present invention thus relates to a calcineurin inhibitor for use in the treatment of a lesional vestibular disorder.

In one embodiment of the invention, the calcineurin inhibitor is cyclosporine A or its derivatives. In one embodiment of the invention, the cyclosporine A derivative is voclosporin.

In one embodiment of the invention, the calcineurin inhibitor is tacrolimus or its derivatives. In one embodiment of the invention, the tacrolimus derivative is pimecrolimus.

In one embodiment of the invention, the calcineurin inhibitor is CN585 (6-(3,4-dichlorophenyl)-4-(N,N-dimethylaminoethylthio)-2-phenyl-pyrimidine).

In one embodiment of the invention, said lesional vestibular disorder is selected from the group consisting of vestibular neuritis, viral neuronitis, labyrinthitis, viral endolymphatic labyrinthitis, drug-induced ototoxicity, Ménière's disease, endolymphatic hydrops, head trauma with lesional vestibular deficits, labyrinthine haemorrhage, chronic or acute labyrinthine infection, serous labyrinthine, barotraumatism, autoimmune inner ear disease, chronic Menière disease, presbyvestibulia, and toxic vestibular impairments.

DETAILED DESCRIPTION

The Inventors made the observation that inhibition of calcineurin leads to the treatment of lesional vestibular disorders in an animal model mimicking clinical pathological mechanisms of said disorders. Without willing to be bound to a theory, the Inventors suggest that excessive calcium influx following cellular insult leads to activation of calcineurin. Pathological calcineurin activation results in cofilin activation, leading to depolymerisation of the cytoskeletal protein actin resulting in cellular swelling and loss of functional synaptic connections. Additionally, calcineurin mediated release of cytochrome c and AIF (apoptosis inducing factor) from mitochondria may lead to respectively caspase-dependent and -independent cell death. Loss of functional synaptic connections and cell death result in vestibular dysfunction. Furthermore, calcineurin induced translocation of NFAT leads to increased recruitment of neurodegenerative inflammatory responses and production of reactive nitrogen species. Therefore, inhibition of calcineurin activity would allow the treatment of lesional vestibular disorders.

One object of the present invention is thus to provide calcineurin inhibitor for use in the treatment of lesional vestibular disorders.

Another object of the present invention is to provide calcineurin inhibitor for use in the treatment of the lesion in a lesional vestibular disorder.

As used herein, the term "treatment" refers to preventing (i.e. keeping from happening), reducing or alleviating at least one adverse effect or symptom of a disease, disorder or condition associated with a deficiency in or absence of an organ, tissue or cell function. Accordingly the aim of the invention is to provide an ending of the lesional vestibular disorders or an amelioration of the subject's condition by restoring the functionality or part of the functionality of the vestibular endorgans and therefore restoring the vestibular functionality. The invention also aims at preventing any lesion to appear or preventing lesions already present to increase.

The present invention thus provides method for treating, protecting, restoring the vestibular neuronal network or the vestibular functionality in a subject affected by a lesional vestibular disorder, said method comprising administering a therapeutically effective amount of calcineurin inhibitors to the subject.

As used herein, the term "lesional vestibular disorder or deficit" refers to vestibular disorders wherein lesions on inner ear cells and/or vestibular nerve are present or will appear during the disorder time course. In this case, the functionality of the vestibule is impaired. Lesional vestibular disorders include:

vestibular disorders wherein an infection inflames the inner ear and/or the vestibular nerve inducing reversible and/or irreversible damages. One example of conditions from this group is vestibular neuritis;

vestibular disorders wherein inner ear fluids are affected (abnormalities in the quantity, composition, and/or pressure of the endolymph), these disorders usually develop lesions during the disease time course. Examples of conditions from this group are Menière's disease and secondary endolymphatic hydrops;

vestibular disorders induced by insults or lesions of the vestibular endorgans. Examples of said conditions are vertigo causes by local ischemia, excitotoxicity, trauma that affect temporal bones or ototoxic insult to vestibular hair cells by drugs such as gentamicin and cisplatin.

Examples of lesional vestibular disorder that are contemplated by the invention include, but are not limited to, vestibular neuritis, viral neuronitis, labyrinthitis, viral endolymphatic labyrinthitis, drug-induced ototoxicity, Ménière's disease, endolymphatic hydrops, head trauma with lesional vestibular deficits, labyrinthine haemorrhage, chronic or acute labyrinthine infection, serous labyrinthine, barotraumatism, autoimmune inner ear disease, presbyvestibulia, toxic vestibular impairments.

In one embodiment, the lesional vestibular disorder is vestibular neuritis.

In one embodiment, the lesional vestibular disorder is viral neuronitis.

In one embodiment, the lesional vestibular disorder is labyrinthitis.

In one embodiment, the lesional vestibular disorder is viral endolymphatic labyrinthitis.

In one embodiment, the lesional vestibular disorder is drug-induced ototoxicity.

In one embodiment, the lesional vestibular disorder is Ménière's disease.

In one embodiment, the lesional vestibular disorder is endolymphatic hydrops.

In one embodiment, the lesional vestibular disorder is head trauma with lesional vestibular deficits.

In one embodiment, the lesional vestibular disorder is labyrinthine haemorrhage.

In one embodiment, the lesional vestibular disorder is chronic or acute labyrinthine infection.

In one embodiment, the lesional vestibular disorder is serous labyrinthine.

In one embodiment, the lesional vestibular disorder is barotraumatism.

In one embodiment, the lesional vestibular disorder is autoimmune inner ear disease.

In one embodiment, the lesional vestibular disorder is presbyvestibulia.

In one embodiment, the lesional vestibular disorder is toxic vestibular impairments.

In one embodiment of the invention, the lesional vestibular disorder is not autoimmune inner ear disease.

According to the invention, lesional vestibular disorders may be identified using MRI for large lesions or by indirect assessment methods allowing the evaluation of the loss of functionality of the vestibule. These methods are generally conducted at ENT clinic/hospitals and include the vestibulonystagmography (VNG), and assessment of the vestibuloocculomotor reflex (VOR) using caloric or rotational tests, heat impulse testing (HIT) or vestibular evoked myogenic potentials (VEMP). The function of the vestibulo-ocular reflex (VOR) is to stabilize the visual image on the retina during displacement. Measurement of this VOR provides a convenient method to investigate the functionality of the vestibular system. Basically, the paradigm is based on monitoring eyes movements by infrared light projection technique (Strupp & Brandt, Seminars In Neurology, 2009, 29(5): 509-519). Patients are sinusoidally oscillated in the dark around their vertical and longitudinal axes in order to evoke horizontal and vertical eye responses. Any functional impairment of the vestibule is associated with alterations in the gain of the evoked VNG. Besides VOR and VNG, posturography methods are used to detect postural deviations of the body that are also related to impairments of the vestibule. Morphofunctional investigations such as functional imaging (MRI or CAT (computerized axial tomography) and derivates) can be used to detect profound lesions within the vestibular endorgans. Specifically adapted VNG, VOR and postural testings are used in animal models of vestibular deficits to evaluate the amplitude of the insults or lesions in the vestibule. Histological studies are also possible using conventional light or electron microscopy on fixed tissue (vestibular ganglia and vestibular endorgans). Such investigations are mostly done in rodents.

As used herein, the term "subject" denotes a mammal, such as a rodent, a feline, a canine, and a primate. Preferably, a subject according to the invention is a human.

In one embodiment, the invention relates to a calcineurin inhibitor for use in the treatment of a lesional vestibular disorder.

In another embodiment, the invention relates to a calcineurin inhibitor for use in a method for restoring vestibular functionality in a subject affected with a lesional vestibular disorder. Said restoration may be evaluated using the VNG or assessment of the VOR as mentioned here above.

As used herein, a "calcineurin inhibitor" refers to any drug or compound that results in inhibition or down regulation of the biological activity associated with the calcineurin or of the calcineurin-NFATc pathway, the calcineurin-cofilin pathway or the calcineurin-BAD pathway.

Calcineurin, also named protein phosphatase 2B (PP2B), is a cytosolic Ser/Thr protein phosphatase, consisting of two subunits: the enzymatic subunit A and the regulatory subunit B. The subunit A contains a calmodulin binding site and an autoinhibitory domain, which blocks the catalytic centre of the enzyme. Binding of $Ca^{2+}$ ions and calmodulin to calcineurin leads to a change of conformation and a subsequent unmasking of the active centre. Calcineurin has the ability to dephosphorylate a broad range of proteins, among which are the actin-depolymerization factor cofilin, the Bcl-2-associated death promoter (BAD) protein and the transcription factors of the NFATc (nuclear factor of activated T cells) family: NFATc1 to NFATc4.

Accordingly, inhibition of the calcineurin activity may be obtained by inhibiting its expression, in particular the expression of one of its subunit. Inhibition of calcineurin expression may be achieved by any means known in the art, e.g. for example by chemically synthesized oligonucleotides such as DNA, RNA, nucleic acid analogue, peptide nucleic acid (PNA), pseudo-complementary PNA (pcPNA), locked nucleic acid (LNA), antisense nucleotides, ribozymes, RNAi, short interfering RNA (siRNA), short hairpin RNA (shRNA), microRNA, miRNA or nucleic acid aptamers.

Alternatively, inhibition of the calcineurin activity may also be obtained by a compound that inhibits the interaction between the calcineurin subunits or between calcineurin and its substrates, e.g. cofilin, BAD or NFAT. Said inhibition of interaction may be achieved by any means known in the art, e.g. for example by small organic molecules, peptides, peptide aptamers or antibodies.

In another embodiment, the calcineurin inhibitor is a drug or compound that inhibits cofilin/BAD/NFAT activity, in particular cofilin/BAD/NFAT dephosphorylation, or that inhibits cofilin/BAD/NFAT expression.

According to the invention, the calcineurin inhibitor may be of various origin, nature and composition. It may be any organic or inorganic substance, such as lipid, peptide, polypeptide, nucleic acid, small molecule . . . , in isolation or in mixture with other substances.

In one embodiment of the invention, the calcineurin inhibitor is a small molecule. Examples of said small molecules are described in Sieber et al. (Cell Communication and Signaling 2009, 7:25), which is herein incorporated by reference, and include, but are not limited to, Cyclosporin A (CsA) and CsA derivatives that are capable to inhibit calcineurin activity such as for example [(R)α-Methylsarcosine$^3$]CsA, [Dimethylaminoethylthiosarcosine$^3$]CsA, [MeBm2t]1-CsA, ISA247 (voclosporin); FK506 (tacrolimus) and derivatives that are capable to inhibit calcineurin activity such as for example FK520 (ascomycin), pimecrolimus (SDZ AM 981, 33-epi-chlor-33desoxy-ascomycin), L-732,531 (32-O-(1-hydroxyethylindol-5-yl)-ascomycin), L-685,818 (FK506BD) and V-10,367; FMPP (4-(fluoromethyl)phenyl phosphate), tyrphostins, norcantharidin, okadaic acid, endothall, kaempferol, barbiturates, 1,5-dibenzoyloxymethyl-norcantharidin, gossypol, Lie120, PD144795, diberufin, dipyridamole, NCI3, INCA compounds, BTPs or 3,5-bis(trifluoromethyl)pyrazoles, BTP1, BTP2 (YM-58483), BTP3, BTP A-285222, ST1959, AM404, UR-1505, Triflusal, rocoglamide derivatives, WIN 53071, trifluoroperazine, KRM-III, caffeic acid phenyl ethyl ester (CAPE), YM-53792, quinazolinediones, pyrrolopyrimidinediones, NFAT-68, NFAT-133, punicalagin, imperatorin, quinolone alkaloids.

In another embodiment of the invention, the calcineurin inhibitor is a peptide. Examples of said peptides are described in Sieber et al. (Cell Communication and Signaling 2009, 7:25), which is herein incorporated by reference, and include, but are not limited to, AID fragments (derived from the autoinhibitory domain of the calcineurin) such as $AID_{424-521}$, $AID_{457-482}$, $AID_{420-511}$, $AID_{328-511}$, 11R-$AID_{457-482}$; PxIxIT peptides (derived from the conserved calcineurin docking motif PxIxIT found in NFATc), VIVIT 16mer oligopeptide, $NFATc2_{106-121}$-SPRIEIT peptide, $AKAP79_{330-357}$ peptide, RCANI peptide, $RCANI-4_{141-197}$-exon7, $RCANI-4_{143-163}$-CIC peptide, LxVPcI peptide, $RCANI-4_{95-118}$-SP repeat peptide, VacA peptide, A238L and $A238L_{200-213}$. Another example of peptides is pS3 peptide (derived from the cofilin phosphorylation domain) (Figge et al. 2012, Mol cell Neurosci, 49(2):196, which is herein incorporated by reference).

In one embodiment of the invention, the calcineurin inhibitor is CsA or CsA derivatives that are capable to inhibit calcineurin activity such as for example [(R)α-Methylsarcosine$^3$]CsA, [Dimethylaminoethylthiosarcosine$^3$]CsA, [MeBm2t]1-CsA, ISA247 (voclosporin).

In one embodiment of the invention the calcineurin inhibitor is FK506 (tacrolimus) or FK506 derivatives that are capable to inhibit calcineurin activity such as for example FK520 (ascomycin), FK523, pimecrolimus (SDZ AM 981, 33-epi-chlor-33desoxy-ascomycin), L-732,531 (32-O-(1-hydroxyethylindol-5-yl)-ascomycin), L-685,818 (FK506BD), L-732-731, 15-0-DeMe-FK-520, meridamycin, 31-O-Demethyl-FK506, V-10,367, L-683,590, L-685, 818, C 18-OH-ascomycin; 9-deoxo-31-O-demethyl-FK506; L-688,617; A-1 19435; AP1903. In one embodiment, the calcineurine inhibitor is not selected from the list consisting of 36-methyl-FK506 and 36-fluoro-FK520.

In one embodiment of the invention, said calcineurin inhibitor is the calcineurin inhibitor VIII/CN585 (6-(3,4-Dichlorophenyl)-4-(N,N-dimethylaminoethylthio)-2-phenyl-pyrimidine).

In one embodiment of the invention, the calcineurin inhibitor is not tropisetron.

In one embodiment of the invention, the calcineurin inhibitor is not ondansetron.

In one embodiment of the invention, the calcineurin inhibitor is a peptide from the conserved regulatory domain of NFAT capable of inhibiting protein-protein interaction between calcineurin and NFAT, as described in US2009/186422, which is herein incorporated by reference. The conserved regulatory domain of NFAT is amino acids residues 396-678 in human NFAT1, 414-696 in human NFAT2, 401-683 in human NFAT2b, 405-686 in human NFAT3, 419-700 in human NFAT4.

In one embodiment of the invention, the calcineurin inhibitor is an LxVP peptide as described in EP1975174, which is incorporated herein by reference. Said LxVP peptide comprises the amino acid sequence R1-L-R2-V-P-R3 wherein R1 is a tyrosine or a phenylalanine, R2 is an alanine or a serine and R3 is not a proline. Preferably, LxVPc1 has the sequence DQYLAVPQHPYQWAK (SEQ ID NO: 1), LxVPc3 has the sequence DQFLSVPSPFTWSKP (SEQ ID NO: 2), and LxVPc4 has the sequence MDYLAVPSPLAWSKA (SEQ ID NO: 3).

In one embodiment of the invention, said calcineurin inhibitor is a BAD inhibitor that is a derivative, intermediate or analog of radicicol or pochonin, as described in WO2009/105755, which is incorporated herein by reference.

In one embodiment of the invention, said calcineurin inhibitor is a cofilin inhibitor that is cucurbitacin E.

In one embodiment of the invention, the calcineurin inhibitor is a shRNA or a siRNA that inhibits the expression of a BAD polypeptide, as described in CA2709132, which is incorporated herein by reference. Examples of shRNA include, but are not limited to, CTCACTACCAAATGTTAAT (SEQ ID NO: 4), GAGTGACCTTCGCTCCACA (SEQ ID NO: 5), GAGTTTGTGGACTCCTTTA (SEQ ID NO: 6), GTGCTCACTACCAAATGTT (SEQ ID NO: 7), GACTTGGACTTGGATGTAA (SEQ ID NO: 8). Examples of siRNA include, but are not limited to, GAUCGGAACUUGGGCAGGG (SEQ ID NO: 9), CAGAGUUUGAGCCGAGUGA (SEQ ID NO: 10), GAGCUCCGGAGGAUGAGUG (SEQ ID NO: 11), UUGUGGACUCCUUUAAGAA (SEQ ID NO: 12).

Another object of the invention relates to a method for the treatment of a lesional vestibular disorder comprising administering a subject in need thereof with a calcineurin inhibitor.

Another object of the invention relates to a method for restoring vestibular functionality in a subject affected with a lesional vestibular disorder comprising administering a subject in need thereof with a calcineurin inhibitor.

Calcineurin inhibitor may be administered in the form of a pharmaceutical composition, as defined below.

Preferably, said calcineurin inhibitor is administered in a therapeutically effective amount.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific inhibitor employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. For instance, the dose of FK506 can be from 0.001 mg/kg/day to 10 mg/kg/day, preferably between 0.01 and 10 mg/kg/day, more preferably between 0.1 and 1 mg/kg/day, by oral administration and between 0.001 and 1 mg/kg/day by intravenous injection, preferably between 0.01 and 0.5 mg/kg/day. In a particular embodiment, the blood FK506 level is comprised between 5 and 40 ng/ml, preferably between 15 and 20 ng/ml. Accordingly, the administered dose of FK506 can be adapted in order to obtain the above-mentioned blood FK506 level. The dose of cyclosporin A as oral formulation (Neoral; Sandimmune) can be from 0.1 mg/kg/day to 10 mg/kg/day, preferably from 0.1 mg/kg/day to 1 mg/kg/day.

The calcineurin inhibitor may be combined with pharmaceutically acceptable excipients, and optionally sustained-release matrices, such as biodegradable polymers, to form therapeutic compositions.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The calcineurin inhibitor can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredients in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

In a particular embodiment, the calcineurin inhibitor may be administered directly in the inner ear through the tympanic membrane. This administration mode may be preferred for introducing a direct and long term effect on the vestibule. Accordingly in a preferred embodiment, the calcineurin inhibitor is administered in a gel formulation to allow a long term release of said antagonist or inhibitor in the inner ear.

The invention will be further illustrated by the following figures and examples. However, these examples and figures should not be interpreted in any way as limiting the scope of the present invention.

EXAMPLES

The present invention is further illustrated by the following examples.

Example 1

Materials and Methods

Animals

Experiments were carried out using 190-220 g adult female Long-Evans rats (CERJ, Le Genest, France) in accordance with the French Ministry of Agriculture regulations and European Community Council directive.

Head Post Surgery

Two inverted 3 mm bolts partially encased in dental acrylic were surgically fixed to the skull of female Long-Evans rats under deep ketamine-xylazine anesthesia using self-tapping surgical screws and cyanoacrylate. Each animal was allowed to recover for 1 week before experiencing 4 training sessions with head fixation (5-10 min) of increasing duration in the week preceding the experiments.

Vestibular Excitotoxic Lesion

Under visual control using a surgical microscope, each rat received transtympanic injections of 50 μL 15 mM kainic acid in physiological serum with 10 mg/mL benzyl alcohol at t=0 h and 25 μL 15 mM kanic acid in physiological serum with 10 mg/mL benzyl alcohol at t=2 h.

Vestibular Deficit Determination

At t=1 h the behaviorally associated vestibular deficits of each transtympanically injected animal was determined using 5 classical criteria each scored on a 0-4 scale: Circling, head-bobbing, degree of head-tilt, tail-hanging reflex deficit and air-righting reflex deficit. Only animals with a total pre-treatment score ≥7 (sum of scores in all 5 criteria) were included in the study.

Infra-Red Videonystagmography

Spontaneous eye-movements were recorded at t=1 h and t=24 h in the dark using an ISCAN ETL-200 infra-red videooculography system under head-fixed conditions. For comparison, spontaneous nystagmus frequency at t=24 h for each group was normalized to the mean spontaneous nystagmus frequency at t=1 h (pre-treatment value).

Calcineurin Inhibitor Treatment

Immediately following behavioral testing and infra-red videoonystagmography at t=1 h, rats received an i.p. injection of either serum (sham treated group) or 2.5 mg/kg FK-506 monohydrate (calcineurin inhibitor treatment group) under double-blind, randomized conditions before being returned to their cage until further manipulation.

Immunohistochemistry

Animals were deeply anesthetized with Pentobarbital (0.4%), then perfused transcardially with heparin PBS (0.01M) followed by a fixative solution (4% paraformaldehyde, 1% picric acid, with 5% sucrose). Temporal bones were postfixed in the same solution before dissection in PBS. Vestibular endorgans were embedded in 4% agarose and 40 μm thick sections were cut with a vibratome (HM650V, Microm). The free-floating sections were permeabilized with 4% Triton X-100 and non-specific binding prevented by pre-incubation in a blocking solution of 0.5% fish gelatin, 0.5% Triton X-100 and 1% BSA. Samples were then incubated overnight with primary antibodies against neurofilament (mouse N52 1:200, Sigma-Aldrich, France) and calcineurin AB (rabbit 1:1000, Swant, Switzerland) diluted in the blocking solution. Specific labeling was revealed with fluorescent secondary antibodies Alexa 488 anti-mouse and Alexa 594 anti-rabbit (both 1:700, Fisher Scientific, Illkirch, France) in the blocking solution. Before mounting, tissue was stained with DAPI (1:5000, Sigma-Aldrich, France). Samples were examined using a laser scanning confocal microscope (LSM 5 LIVE DUO, Zeiss). Final image processing was done with Adobe Photoshop software (San Jose, Calif.).

Data Analysis

The spontaneous nystagmus frequency in videooculography traces recorded at t=1 h (pre-treatment) and t=24 h (chronic deficit) was determined using custom routines written in MatLab R2011b (The Mathworks, Natick, Mass.). The determined spontaneous nystagmus frequencies at t=24 h were normalized to the group (sham treated group/FK-506 group) mean frequency at t=1 h. Statistically significant differences were determined using Student's t-test in SigmaPlot 11 (SyStat Software Inc., San Jose, Calif.). Data were visualized in SigmaPlot 11 (SyStat Software Inc., San Jose, Calif.).

Specific Inhibition of Calcineurin Activity Reduces Excitotoxic Vestibular Damage in Vivo Damage to the peripheral sensory vestibular system in pathologies such as Meniere's disease (hyperexcitability), vestibular neuritis (inflammation), vertebrobasilar stroke (ischemia) and traumatic head injury occurs through mechanisms involving excessive intracellular calcium accumulation leading to deleterious activation of secondary signaling cascades.

In an animal model mimicking clinical pathological mechanisms using transtympanic application of the excitotoxin kainic acid (kainate) to the inner ear, we here demonstrate that inhibition of the calcium/calmodulin activated phosphatase calcineurin leads to significant reduction of the lasting spontaneous nystagmus in animals treated with FK-506 (tacrolimus) subsequent to the initiation of the vestibular insult.

Calcineurin Expression in the Peripheral Vestibular System

Figure 1:
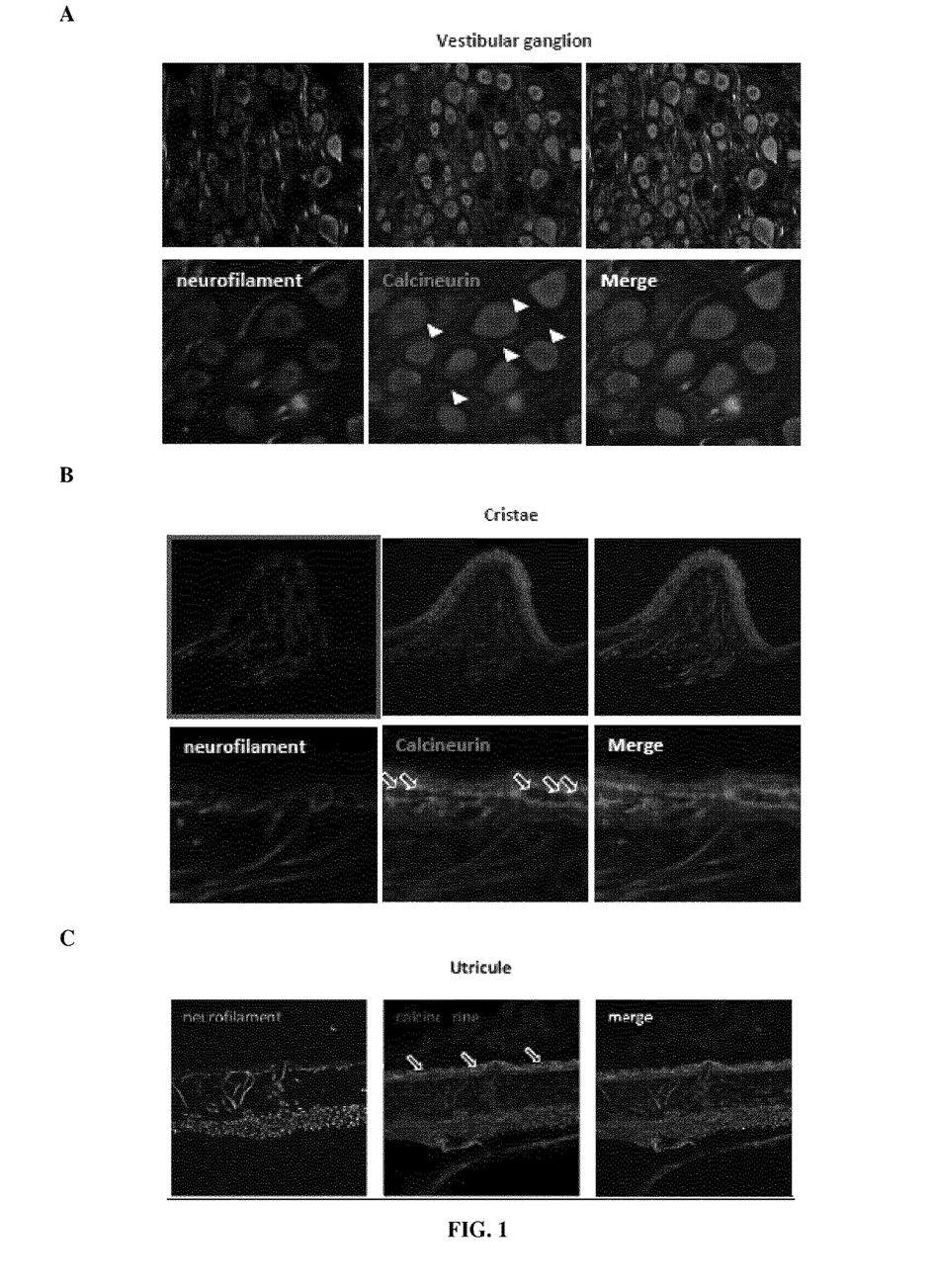
FIG. 1 shows the calcineurin expression in the peripheral vestibular system: in vestibular ganglion (A), in cristae (B) and in utricule (C).

FIG. 1A shows that in the vestibular ganglion, calcineurin (red) is expressed in the somata of primary vestibular neurons (arrowheads) expressing the neuron specific structural protein neurofilament (green). Nucleii are labeled with DAPI (blue).

FIG. 1B shows that in the vestibular cristae (sensory epithelium of the semicircular canals), calcineurin (red) is expressed at the level of the sensory hair cells (open arrows). Nucleii are labeled with DAPI (blue).

FIG. 1C shows that in the utricule, calcineurin (red) is expressed at the level of the sensory hair cells (open arrows). Nucleii are labeled with DAPI (blue).

Figure 2:
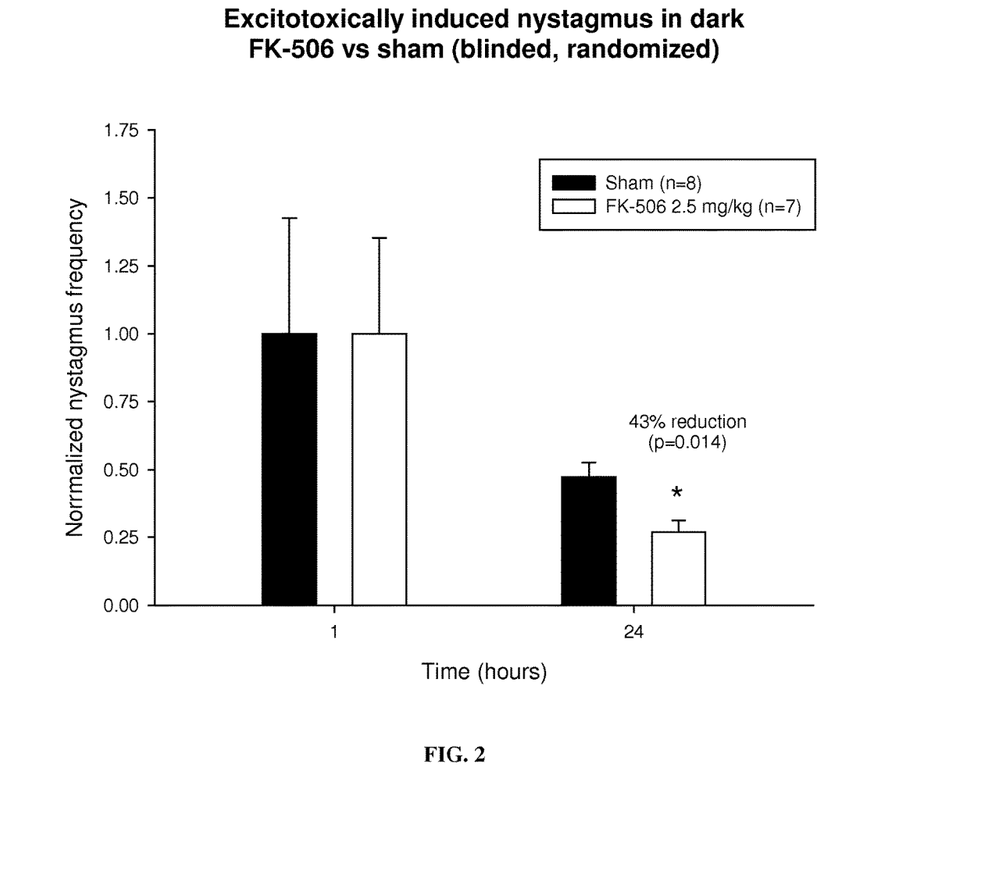
FIG. 2 is a histogram showing the significant protective effect of post-insult 2.5 mg/kg systemic FK-506 (n=7, white histogram bars) vs sham (n=8, black histogram bars) treatment on excitotoxically induced lasting vestibular deficits.

Reduction of Chronic Spontaneous Nystagmus Frequency by the Calcineurin Inhibitor FK-506 after Excitotoxic Insult FIG. 2 shows that; at t=24 h, the normalized chronic spontaneous nystagmus frequency of the FK-506 treated group was 26.9±11.8%. This is significantly different from the 47.2±15.2% normalized chronic spontaneous nystagmus frequency of the sham treated group at t=24 h (p=0.014). This demonstrates that a single systemic (i.p.) injection of the calcineurin inhibitor FK-506 (tacrolimus) at 2.5 mg/kg significantly reduces lasting vestibular deficits (quantified as spontaneous nystagmus in the dark) following excitotoxic insult by 43% under double-blind randomized conditions.

Example 2

Methods

Animals

All experiments were performed using 220-250 g female Long-Evans rats (CERJ, Le Genest, France) in accordance with the French Ministry of Agriculture regulations and European Community Council Directive no. 86/609/EEC, OJL 358.

Headpost Surgery

Following i.p. administration of 100 mg/kg ketamine and 8 mg/kg xylazine, a headpost for immobilization during videooculography recordings was surgically fixated to the skull of each animal under deep anesthesia ascertained by lack of withdrawal reflex following hindlimb pinch: Following sagittal incision of the scalp, a plastic ring (15 o/d mm×10.5 i/d mm×5 mm height; Banbury Plastic Fittings, Banbury, UK) was positioned around four 4.7 mm self-tapping bone-screws (Fine Science Tools, Heidelberg, Germany) fixed into the skull in a rectangular configuration. Cyanoacrylate adhesive was applied to the exposed skull inside the ring and two inverted 3 mm bolts fixed on the sagittal midline using dental acrylic. Antiseptic solution (Betadine) was applied to the exposed scalp incision and following recovery from anesthesia under observation, the animal was returned to the home cage.

Headrestraint Adaptation

One week after headpost surgery, each animal experienced four training sessions with head fixation following mild isoflurane anesthesia: The animal was placed in a soft "snuggle"-restraint (Lomir Biomedical, Malone N.Y., USA) exposing only the head. The two inverted bolts of the headpost were fixed firmly to the headrestraint on the videooculography stage for training durations 5 min, 7 min, 7 min and 10 min (throughout one week) to reduce anxiety during subsequent recordings.

Unilateral Vestibular Deficit Induction

An excitotoxic unilateral vestibular insult was delivered under isoflurane anesthesia, using 50 µL transtympanic injections of 20 mM kainic acid (Abcam Biochemicals, Cambridge, UK) in physiological serum containing the round window permeabilizer benzyl alcohol (Sigma-Aldrich, Lyon, France) at 10 mg/mL into the left middle ear at t=0 h. The animal was left to recover from anesthesia on the right side under observation.

Cyclosporin A Treatment

Pharmacological treatment with 50 mg/kg of the calcineurin inhibitor Cyclosporin A (Abcam Biochemicals, Cambridge, UK) administered i.p. in a solution of 20% Cremophor EL/2% EtOH/1% Tween 80/77% physiological serum was carried out under blind, randomized conditions with the blinded experimenter administering treatment to each animal immediately after functional pre-treatment characterization at t=1 h.

Behavioral Testing

At t=1 h (pre-treatment) and 24 h after the initial excitotoxic insult, the vestibular deficit was assessed using the combined score of 5 behavioral deficit criteria characteristic for unilateral vestibular injury, each scored on a discrete scale indicating normal behavior (0) to maximal impairment (4): circling, head-bobbing, tail-hanging reflex, air-righting reflex and degree of lateral head-tilt. Any animal displaying stereotypical symptoms of beginning kainate-induced seizure activity was immediately euthanized using lethal pentobarbital injection and all data excluded from analysis.

Videonystagmography Recordings

At t=1 h (pre-treatment) and 24 h after the initial excitotoxic insult, spontaneous nystagmus was recorded using a computer controlled infrared videooculography setup for rodents (ETL-200, ISCAN Inc., Woburn Mass., USA). Eye movements detected based on pupil position were recorded for 2 min at each time-point and stored offline in ASCII format for subsequent analysis.

Data Analysis and Statistics

Determination of spontaneous nystagmus frequency from videonystagmography recordings for each animal, time-point and treatment condition was carried out in MatLab (MathWorks, Natick, Mass.) using custom written routines. All plotting and statistical analysis of nystagmus data was performed in SigmaPlot (Systat, Chicago, Ill.) using nystagmus frequencies normalized to pre-treatment group mean and using Student's t-test. Any detected differences were considered significant for $p<0.05$. Data values are expressed as mean±s.e.m.

Results: Cyclosporin a Treatment Reduces Excitotoxically Induced Vestibular Deficits Under blinded and randomized conditions, animals with a moderate to severe functional vestibular deficits (deficit score ≥7) at t=1 h received either Cyclosporin A (50 mg/kg, i.p.) or the corresponding sham treatment solution (see Methods).

Figure 3:
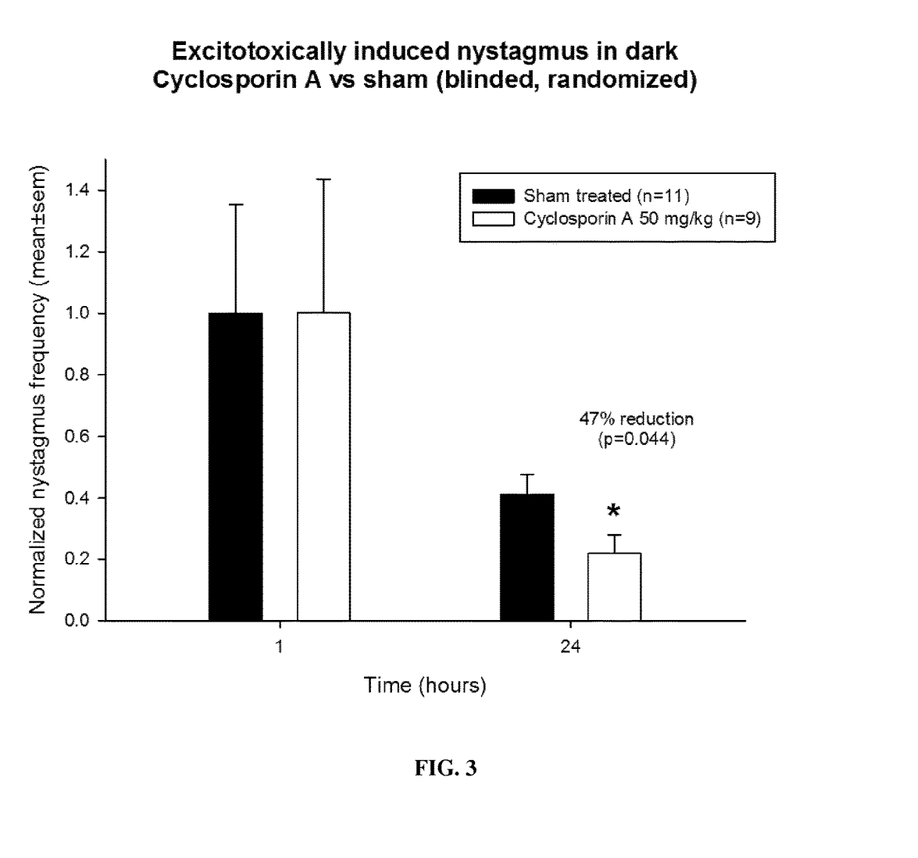
FIG. 3 is a histogram showing the significant protective effect of post-insult 50 mg/kg systemic Cyclosporin A (n=9, white histogram bars) vs sham (n=11, black histogram bars) treatment on excitotoxically induced lasting vestibular deficits.

The recorded spontaneous frequencies were determined using custom software routines and the pre-treatment (t=1 h) and lasting (t=24 h) plotted after normalization to the group pre-treatment mean value (FIG. 3).

FIG. 3 shows that sham treated animals (n=11, black histogram bars) retained 41.3±6.5% of the acute (t=1 h) nystagmus frequency under dark conditions at t=24 h, while animals receiving 50 mg/kg Cyclosporin A (n=9, white histogram bars) only displayed a lower lasting nystagmus (at t=24 h) frequency at 21.9±5.9% of the acute pre-treatment value.

This statistically significant (p=0.044) 47% reduction of lasting vestibular deficits at t=24 h (as determined by spontaneous nystagmus frequency under dark conditions) clearly demonstrates the protective treatment effect of systemic calcineurin inhibitor administration in a rat model of lesional vestibular deficits.

The invention claimed is:

1. A method for restoring or ameliorating the functionality of the vestibular endorgans in a subject affected by a lesional vestibular disorder, comprising the step of systemically administering to the subject a therapeutically effective amount of a pharmaceutical composition consisting essentially of a calcineurin inhibitor,
   wherein the lesional vestibular disorder is selected from the group consisting of drug-induced ototoxicity and excitotoxicity,
   wherein the calcineurin inhibitor is selected from the group consisting of tacrolimus, cyclosporin A, CN585 and their derivatives; and
   wherein administration of the calcineurin inhibitor restores or ameliorates the functionality of the vestibular endorgans in the subject affected by a lesional vestibular disorder.

2. The method according to claim 1, wherein the calcineurin inhibitor is tacrolimus or its derivatives.

3. The method according to claim 2, wherein the calcineurin inhibitor is a tacrolimus derivative further defined as pimecrolimus.

4. The method according to claim 1, wherein the calcineurin inhibitor is cyclosporine A or its derivatives.

5. The method according to claim 4, wherein the calcineurin inhibitor is a cyclosporine A derivative.

6. The method according to claim 1, wherein the calcineurin inhibitor is CN585 (6-(3,4-dichlorophenyl)-4-(N,N-dimethylaminoethylthio)-2-phenyl-pyrimidine).

7. The method according to claim 2, wherein the tacrolimus derivative is selected from the group consisting of ascomycin, FK523, pimecrolimus, L-732,531, L-685,818, L-732-731, 15-0-DeMe-FK-520, meridamycin, 31-O-Demethyl-FK506, V-10,367, L-683,590, L-685,818, C18-OH-ascomycin, 9-deoxo-31-O-demethyl-FK506, L-688,617, A-1 19435 and AP1903.

8. The method according to claim 4, wherein the cyclosporin A derivative is selected from the group consisting of [(R)α-methylsarcosine$^3$] cyclosporin A, [dimethylaminoethylthiosarcosine$^3$] cyclosporin A, [MeBm2t]1-CsA and voclosporin.

9. The method according to claim 1, wherein a single acute therapeutically effective amount of the pharmaceutical composition consisting essentially of a calcineurin inhibitor is administered to the subject.

* * * * *